US008530708B2

(12) United States Patent
Wang et al.

(10) Patent No.: US 8,530,708 B2
(45) Date of Patent: *Sep. 10, 2013

(54) PROCESSES FOR SELECTIVE DEHYDROHALOGENATION OF HALOGENATED ALKANES

(75) Inventors: Haiyou Wang, Amherst, NY (US);
Hsueh Sung Tung, Getzville, NY (US);
Sudip Mukhopadhyay, Berkeley, CA (US)

(73) Assignee: Honeywell International Inc., Morristown, NJ (US)

( * ) Notice: Subject to any disclaimer, the term of this patent is extended or adjusted under 35 U.S.C. 154(b) by 647 days.

This patent is subject to a terminal disclaimer.

(21) Appl. No.: 11/588,465

(22) Filed: Oct. 27, 2006

(65) Prior Publication Data

US 2007/0129579 A1   Jun. 7, 2007

Related U.S. Application Data

(63) Continuation of application No. 11/118,503, filed on Apr. 29, 2005, now Pat. No. 7,345,209, and a continuation of application No. 10/694,272, filed on Oct. 27, 2003, now Pat. No. 7,230,146, and a continuation of application No. 10/626,997, filed on Jul. 25, 2003, now Pat. No. 7,592,494.

(60) Provisional application No. 60/763,086, filed on Jan. 27, 2006, provisional application No. 60/733,355, filed on Nov. 3, 2005.

(51) Int. Cl.
*C07C 17/25* (2006.01)

(52) U.S. Cl.
USPC ............ 570/156; 570/155; 570/157; 570/136

(58) Field of Classification Search
None
See application file for complete search history.

(56) References Cited

U.S. PATENT DOCUMENTS

| 4,138,355 | A | * | 2/1979 | Ferstandig ............... 252/183.14 |
| 4,876,405 | A | * | 10/1989 | Gervasutti ..................... 570/156 |
| 5,180,860 | A | * | 1/1993 | Fernandez et al. ............ 570/157 |
| 5,672,803 | A | | 9/1997 | Smith et al. |
| 5,679,875 | A | | 10/1997 | Aoyama et al. |
| 6,369,284 | B1 | | 4/2002 | Nappa |
| 6,548,719 | B1 | * | 4/2003 | Nair et al. ..................... 570/157 |
| 6,734,332 | B1 | | 5/2004 | Slaugh et al. |
| 7,230,146 | B2 | | 6/2007 | Merkel et al. |
| 2004/0119047 | A1 | | 6/2004 | Singh et al. |
| 2005/0090698 | A1 | | 4/2005 | Merkel et al. .................. 570/155 |

FOREIGN PATENT DOCUMENTS

WO  2005012212 A2  2/2005

OTHER PUBLICATIONS

U.S. Appl. No. 10/694,273, filed Oct. 27, 2003, Singh et al.
Kiyoshi Endo et al., "Monomer-Isomerization Polymerization-XXVI. The Case of 2-Butene in the Presence of Isobutene with Ziegler-Natta Catalyst," Eur. Polym. J., vol. 28, No. 2, pp. 153-157 (1992).

* cited by examiner

*Primary Examiner* — Yevegeny Valenrod
(74) *Attorney, Agent, or Firm* — Bruce O. Bradford

(57) ABSTRACT

Disclosed are processes for producing halogenated olefins, and preferably tetrafluorinated propene(s), from one or more alkanes having both fluorine substituents and non-fluorine substituents, preferably with a high degree of conversion and selectivity. Preferably the process comprises the use of a catalyzed reaction in which the catalyst is selected from the group consisting of activated carbons, halogentated mono- and di-valent metal oxides, mono- and di-valent Lewis acid metal halides, zero-valent metals, and combinations of these.

11 Claims, No Drawings

PROCESSES FOR SELECTIVE DEHYDROHALOGENATION OF HALOGENATED ALKANES

CROSS REFERENCE TO RELATED APPLICATIONS

This application is related to and claims the priority benefit of U.S. patent application Ser. No. 10/694,272, filed on Oct. 27, 2003 (now U.S. Pat. No. 7,230,146), which is incorporated herein by reference.

This application also is related to and claims the priority benefit of U.S. patent application Ser. No. 10/626,997, filed on Jul. 25, 2003 (now U.S. Pat. No. 7,592,494), which is incorporated herein by reference.

This application is also related to and claims the priority benefit of U.S. patent application Ser. No. 11/118,503, filed on Apr. 29, 2005 (now U.S. Pat. No. 7,345,209), which is incorporated herein by reference.

This application is related to and claims the priority benefit of provisional application 60/733,355, filed on Nov. 3, 2005 (expired), which is incorporated herein by reference.

This application is also related to and claims the priority benefit of provisional application 60/763,086 filed on Jan. 27, 2006 (expired), which is incorporated herein by reference.

Also incorporated herein by reference are of the following U.S. Applications.

FIELD OF THE INVENTION

The present invention relates to processes for the selective dehydrohalogenation of certain halogenated alkanes to produce halogenated olefins. In certain aspects, the invention relates to processes for the conversion of C2-C6 hydrochlorofluoroalkanes to C2-C6 fluoroolefins.

BACKGROUND OF THE INVENTION

It is known to produce certain hydrofluoroolefins (HFOs) by the catalytic dehydrochlorination of certain hydrochlorofluorocarbons. For example, co-pending U.S. Patent Publication 2005/0090698, which is assigned to the assignee of the present invention and which is incorporated herein by reference, discloses processes involving the following reaction:

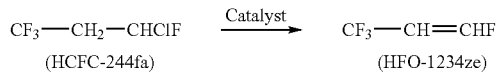

(HCFC-244fa)     (HFO-1234ze)

This publication indicates that these reactions may proceed by thermal decomposition, either in the presence or the absence of catalyst. With respect to the use of catalysts, this publication indicates that suitable catalysts include transition metal halides and oxides in general, and mentions specifically $FeCl_2$, $FeCl_3$, $NiCl_2$ and $CoCl_2$.

Among the halogenated olefins, tetrafluoropropenes (including HFO-1234ze) are known to be useful in numerous applications. For example, U.S. patent application Ser. No. 10/694,273, which is assigned to the assignee of the present invention and incorporated herein by reference, discloses the use of HFO-1234ze ($CF_3CH{=}CFH$) as a refrigerant with low global warming potential and also as a blowing agent for use in connection with the formation of various types of foams. In addition, $CF_3CH{=}CFH$ can also be functionalized to variety of compounds useful as intermediates for making industrial chemicals.

Applicants have come to recognize that many of the current and prior processes for producing halogenated olefins, and in particular tetrafluorinated propene, produce a mixture of olefins which includes, in addition to the desired hydrofluorinated olefins, a substantial proportion of olefins that have fluorine and chlorine substituents. As a result, applicants have discovered a need for processes which are capable of forming hydrofluorinated olefins with a high degree of conversion and selectivity.

SUMMARY

In one aspect of the present invention, applicants have come to recognize that prior processes for producing tetrafluoroolefins in general, and tetrafluoropropenes in particular, suffer as a result of a hereto for unrecognized need for a process in general, and catalysts in particular, capable of preferentially and selectively producing tertrafluorinated olefins (preferably tetrafluoropropene) from alkane reactants that are both fluorinated and halogenated with at least one other halogen, preferably chlorine. Accordingly, applicants have developed preferred processes for the conversion of C2-C6 alkanes that are both chlorinated and fluorinated, with a degree of chlorine substitution of N and a degree of fluorine substitution of M to C2-C6 olefins having a degree of chlorine substitution of N−1 and a degree of fluorine substitution of M.

DETAILED DESCRIPTION OF PREFERRED EMBODIMENTS

Applicants have found that many prior and current processes which involve efforts to form certain fluorinated olefins by dehydrohalogenation of alkanes that are both chlorinated and fluorinated produce a substantial proportion of reaction product in which one or more fluorine substituents is eliminated. By way of example, applicants have come to realize that prior and current processes for the conversion of HFC-244fa to HFO-1234ze produce substantial quantities of at least one olefin containing chlorine substituents as follows:

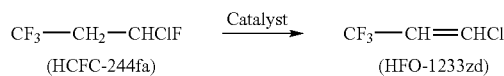

(HCFC-244fa)     (HFO-1233zd)

Applicants have found that careful and judicious selection of the parameters and conditions by which the reaction takes place, including but not limited to catalyst selection, type and/or amount, and/or reaction temperature, can be used according to the present invention to produce relatively high levels of conversion and/or selectivity of the alkane to the desired fluorinated olefin.

Preferred process aspects of the invention involve exposing alkanes that are both chlorinated and fluorinated, particularly one or more alkanes having from two to six carbon atoms, with a degree of chlorine substitution of N and a degree of fluorine substitution of M, to conditions effective to convert at least about 5 percent, more preferably at least about 20 percent, and even more preferably at least about 70% of such alkanes to olefins having a degree of chlorine substitution of a N−1 and a degree of fluorine substitution of M.

In preferred embodiments the alkane reactant in accordance with the present invention is a compound in accordance with Formula (I) below:

$$CF_3CHYCHFY \qquad (I)$$

where Y is H or a halogen other than F, provided that at least one of said Y is H. In such embodiments, it is also highly preferred that the reaction product comprises a compound of Formula (II)

$$CF_3CX\!=\!CHX \qquad (II)$$

where one of said X is H and the other of said X is F.

According to preferred aspects of the present invention, the present processes involve reacting compounds in accordance with Formula (I) under conditions effective to achieve a conversion of the Formula (I) compounds of at least about 5%, more preferably at least about 20%, and even more preferably at least about 70%. Furthermore, preferred aspects of the present processes involve reacting compounds in accordance with Formula (I) under conditions effective to achieve a selectivity to compounds of Formula (II) of at least about 50%, more preferably at least about 70%, and even more preferably at least about 80%. In highly preferred embodiments, the conversion of the Formula (I) compounds is at least about 80%, with a selectivity to compounds of Formula (II) of about 90% or greater.

In preferred embodiments the Formula (I) compound comprises, and preferably consists essentially of, HCFC-244fa and the Formula (II) compound comprises HFO-1234ze.

One important element of such preferred embodiments derives from the discovery by applicants that certain catalysts, when employed in accordance with the teachings contained herein are capable of effectively achieving such high conversion and selectivity levels for such reactions.

Thus, in preferred embodiments the conditions effective to achieve the desired high levels of conversion and selectivity include exposing the feed containing a reactant in accordance with the present invention, preferably a compound of Formula (I) to a catalyst selected from the group consisting of activated carbons and/or metal-based catalyst. For embodiments in which one or more metal-based catalysts are used, it is preferred that the metal based catalyst comprises, and preferably is selected from the group consisting of, halogentated mono- and di-valent metal oxides, mono- and di-valent Lewis acid metal halides, zero-valent metals, and combinations of these. Preferably the present processes including conducting the reaction under reaction conditions, including reaction temperature and residence time, effective to convert at least about 5%, more preferably at least about 20%, and even more preferably at least about 70%, of the reactant compound to one or more of the desired fluorinated olefin, as described herein. Although it is contemplated that the process and catalyst aspects of the present invention may be readily adapted for use in accordance with the formation of fluoroolefins generally, in preferred aspects the present methods and catalysts are adapted for use in connection with transformation of alkanes having three carbon compounds, and more particularly such three-carbon compounds having only fluorine and chlorine substituents.

It is contemplated that a wide variety of process streams may be utilized as the feed to the preferred reaction step of the present invention. For example, in certain embodiments of the present invention the feed stream which contains such alkanes may be include product streams, or fractions thereof, from upstream unit operations or processes, and such streams may be used, either with or without further processing, as the reactant stream in accordance with the present invention. Alternatively, the desired reactants may be purchased from readily available commercial sources.

It is contemplated that the relative amount of the alkane reactant in the feed stream to the conversion step may vary widely within the scope of the present invention. For example, it is contemplated, although not presently preferred, that the feed stream to the conversion step may contain relatively low concentrations, for example less than about 50% by weight or perhaps even as little as 10% by weight, of the alkane of the present invention. In general, however, it is preferred that the reactant feed stream contains relatively high concentrations of the alkane of the present invention. Thus, in preferred embodiments, the feed stream in accordance with preferred aspects of the present invention comprises at least about 50% by weight of the alkane, preferably 50% by weight of compounds in accordance with Formula (I), more preferably at least about 80% by weight, and even more preferably at least about 95% by weight of such compounds.

It is also contemplated that a wide variety of other molecules and materials which make up the balance of the feed stream to the reaction step of the present invention may be present in the feed stream without having a deleterious effect on the preferred conversion and selectivity features of the present invention.

It is contemplated that the conversion step may be preformed using a wide variety of process parameters and process conditions in view of the overall teachings contained herein. However, it is preferred in many embodiments of the present invention that this reaction step comprises a gas phase reaction in the presence of catalyst as described herein.

Applicants have found that such highly desirable levels of conversion and selectivity, and particularly and preferably from feed streams as described herein, can be achieved by the proper selection of operating parameters, including, but not necessarily limited to, catalyst type, reaction temperature, reaction pressure, and reaction residence time. Preferred aspects of each of these parameters are described below.

Applicants have found that four general types of catalysts are highly desirable and effective, when used in accordance with teachings contained herein, to achieve the aforesaid high level of conversion and selectivity. More specifically, in preferred embodiments the catalyst is selected from the group consisting of activated carbons, halogentated mono- and/or di-valent metal oxides, mono- and/or di-valent Lewis acid metal halides, zero-valent metals, and combinations of these.

In general, it is preferred that the catalyst of the present invention comprise, and preferably consists essentially of, one or more components selected from the group consisting of activated carbons, alkali metals (metals in Group IA of the periodic table), alkali earth metals (metals in Group IIA of the periodic table), and transition metals contained in Group VIIIA, Group IB and Group IIB of the periodic table. With respect to activated carbons, it is generally preferred to use activated carbon having a total concentration of $Al^{3+}$ of less than about 8000 ppm, a total concentration of $Fe^{3+}$ of less than about 8000 ppm, and preferably the total cumulative concentration of $Al^{3+}$ and $Fe^{3+}$ of less than about 8000 ppm.

With respect to alkali metals, it is generally preferred to use one or more of such metals having an atomic number of from about 3 to about 56. With respect to alkali earth metals, it is generally preferred to use such metals having an atomic number of from about 12 to about 55. With respect to transition metals, it is generally preferred to use such metals having an atomic number of from about 26 to about 30.

With respect to catalysts based upon zero valent or neutral metals, it is preferred that the metal component comprises, and preferably consists essentially of, one or more metals selected from transition metals, more particularly transition metals contained in Group VIII and Group IB of the periodic table, and even more preferably transition metals having an atomic number of from about 26 to about 29. As used herein, reference to the periodic table means the CAS version of the Periodic Table of Elements.

It is contemplated that in certain preferred embodiments the highly desirable results described are best obtained with the use of activated carbons and one or more metal-based catalysts in which the metal(s) are in an oxidation state of 0, +1 or +2. It is preferred in certain embodiments that the metals are used in accordance with the following oxidations states:

$Li^+$
$Na^+$
$K^+$
$Rb^+$
$Cs^+$
$Mg^{2+}$
$Ca^{2+}$
$Sr^{2+}$
$Ba^{2+}$
$Fe^{2+}$
$Co^{2+}$
$Ni^{2+}$
$Cu^{2+}$
$Zn^{2+}$

In general, any halogen can be used as the component that is included in the preferred metal oxide and metal halide catalyst of the present invention. For catalysts that are halogenated metal oxides (which are sometimes referred to herein for convenience as HMO catalysts), the catalyst preferably comprises a fluorinated and/or chlorinated metal oxide. The agent and conditions used to treat the metal oxide to form the HMO catalyst can vary widely within the scope of the present invention. It is preferred in certain embodiments that the metal oxide be treated with one or more of the following halogenating agents: HF, $F_2$, HCl, $Cl_2$, HBr, $Br_2$, HI, $I_2$ and combinations of these. In certain highly preferred embodiments, the halogenating agent comprises one or more of HF, $F_2$, HCl, $Cl_2$, HBr, $Br_2$, and combinations of these, and even more preferably HF, $F_2$, HCl, $Cl_2$ and combinations of these, and even more preferably HF, $F_2$, and combinations of these.

For catalysts that are Lewis Acid metal halides (which are sometimes referred to herein for convenience as LA catalysts), the catalyst is preferably a metal fluoride, a metal chloride, or combinations of these. In general, any coordinating component can be used as the component that is included in such catalysts of the present invention. It is preferred, however, that Lewis Acid halide comprises a Lewis Acid halide in which the halogen component is selected from F, Cl, Br, I and combinations of these, more preferably F, Cl, Br and combinations of these, even more preferably F, Cl and combinations of these, and most preferably F. In certain highly preferred embodiments, the Lewis Acid catalyst is a Lewis Acid halide, preferably a fluoride, formed from a transition metal, and even more preferably a Lewis Acid halide formed from a transition metal selected from the group consisting of Li, Na, K, Mg, Ni and combinations of these. The agent and conditions used to form the Lewis Acid catalyst can vary widely within the scope of the present invention. It is preferred in certain embodiments that the LA catalyst be formed, for example, by dissolving in an aqueous halogen salt, followed by evaporation and calcination. In one particular, but not limiting example, the process of forming the catalyst comprises 1) dissolving quantities of metal hydroxides, oxides, and/or carbonates, preferably separately, in aqueous HF solution (preferably in 49% aqueous HF solution), with mixing in a Teflon® container; 2) evaporation of the solution to dryness; 3) calcining the dried sample at an elevated temperature for a sufficiently long period, preferably in the presence of inert gas, such as $N_2$; and 4) optionally but preferably forming particles of the material so produced, preferably by grinding, to a fine powder, preferably with palletizing the powder into desired shapes.

With respect to neutral metal catalysts (which are sometimes referred to herein for convenience as NM catalysts), it is generally preferred that the catalyst include one or more transition metals, preferably a transition metal selected from the group consisting of Fe, Co, Ni, Cu and combinations of these.

The particular form of the catalyst can also vary widely. For example, the catalysts of this invention may contain other components, some of which may be considered to improve the activity and/or longevity of the catalyst composition. The catalyst may contain other additives such as binders and lubricants to help insure the physical integrity of the catalyst during granulating or shaping the catalyst into the desired form. Suitable additives, may include, by way of example but not necessarily by way of limitation magnesium stearate, carbon and graphite. When binders and/or lubricants are added to the catalyst, they normally comprise about 0.1 to 5 weight percent of the weight of the catalyst.

Furthermore, the metal-based catalyst may be used in a form where it is either unsupported or supported on a substrate, or in some cases a combination of these forms. It is contemplated that all types of supports know to those skilled in the art are useful in accordance with the present invention. By way of example, any of the catalysts mentioned herein may be supported on one or more materials, including but not necessarily limited to the following: carbon; activated carbon; graphite; fluorinated graphite; and combinations of any two or more of these.

In general, it is not preferred to conduct a further or separate activation step for catalysts consisting of activated carbon. However, for metal based catalyst, it is sometimes preferred to activate such catalysts prior to use, preferably by HF treatment for HMO and LA catalysts or $H_2$ treatment for NM catalysts at elevated temperatures. After use for a period of time in the process of this invention, the activity of the catalyst may decrease. When this occurs, the catalyst may be reactivated. Reactivation of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days, followed by either HF treatment at temperatures of from about 25° C. to about 400° C., preferably from about 200° C. to about 350° C., for HMO and LA catalysts or $H_2$ treatment at temperatures of from about 100° C. to about 400° C., preferably from about 200° C. to about 350° C., for NM catalysts. Alternatively, reactivation of catalyst can be accomplished by co-feeding an oxidizing or reducing agent with the raw material to the reactor.

It is also contemplated that the present processes, in view of the overall teachings contained herein, may be adaptable for use in accordance with a wide variety of reaction temperature conditions. For example it is contemplated that the reaction temperature in preferred embodiments may be from about 100° C. to about 600° C. As used herein, the term "reaction temperature" refers to the average temperature in the catalyst bed, unless otherwise indicated. In certain preferred embodiments, the reaction temperature is preferably from about 200° C. to about 450° C., and even more preferably from about 300° C. to about 400° C.

Although a wide variety of temperatures is generally adaptable for use in connection with the present invention, applicants have surprisingly found that exceptional performance, in terms of conversion and/or selectivity, and preferably both, can be achieved by the use of reaction temperatures within the preferred range of from about 300° C. to less than about 400° C., and even more preferably from about 325° C. to about 375° C. While it is contemplated that these preferred ranges have application generally to conversion reactions in accordance with the present invention, such ranges produce in certain embodiments especially exceptional results, for example in connection with a conversion of HCFC-244fa to HFO-1234ze.

It is also contemplated that a wide variety of pressures may be used in connection with the processes of the present invention. Nevertheless, in certain preferred embodiments, the reaction is carried out under pressure conditions ranging from about a vacuum of about 5 torr to about 200 psig.

It is also contemplated that a wide variety of contact times for the preferred reactions of the present invention may be used. Nevertheless, in certain preferred embodiments, the residence time is preferably from about 0.5 seconds to about 600 seconds.

In preferred aspects of the present invention, the reactant to be converted is contained in a feed stream, and the converting step includes providing one or more reaction vessels, at least one of which preferably contains catalyst of the present invention and introducing the feed stream into the vessel(s) under conditions effective to achieve the desired conversion. It should be appreciated that the term "stream" as used herein is not limited to the singular, and it is contemplated that in certain embodiments separate streams be combined outside the vessel and then introduced to the vessel together, or in other embodiments separate streams might constitute the reactor feed, each of which is introduced into the vessel(s) at different times and/or at different locations. This same convention has been used and applies herein throughout to all use of the term "stream" herein, unless specifically indicated otherwise.

The following examples are given as specific illustrations of the invention. It should be noted, however, that the invention is not limited to the specific details set forth in the examples.

EXAMPLES

Example 1

244fa Dehydrohalogenation Over Activated carbons

In Example 1, two kinds of activated carbons were used as dehydrohalogenation catalysts. 20 cc of each activated carbon was used. HCFC 244fa ($CF_3CH_2CHClF$) was passed over each catalyst at a rate of 12 g/h at a temperature of 350° C. As shown in Table 1, both activated carbons provided a selectivity to HFO=1234ze (cis and trans combined, hereinafter referred to t/c-1234ze) higher than 70% and a selectivity to HFO-1234zd (cis and trans combined, hereinafter referred to a t/c-1233zd), lower than 30%, indicating those activated carbons are more active for HCFC-244fa dehydrochlorination than its dehydrofluorination. It is also noted that the sample with lower concentration of $Al^{3+}$ and $Fe^{3+}$ exhibited much higher selectivity to t/c-1234ze.

TABLE 1

| | HCFC-244fa dehydrohalogenation over various activated carbons at 350° C. | | | | | |
|---|---|---|---|---|---|---|
| | Ion concentration, ppm | Conversion, % | Selectivity, % | | | |
| Sample No. | $Al^{3+} + Fe^{3+}$ | 244fa | t/c-1234ze | 245fa | t/c-1233zd | unknown |
| 1 | <40 | 99.3 | 95.5 | 0.0 | 3.5 | 1.0 |
| 2 | 8556 | 96.3 | 71.0 | 0.6 | 27.5 | 0.9 |

Example 2

HCFC-244fa Dehydrohalogenation Over Metal chloride Catalysts

In Example 2 a series of mono-, bi-, and tri-valent metal chlorides were used as dehydrohalogenation catalysts. 20 cc of each metal chloride catalyst was used. HCFC-244fa was passed over each catalyst at a rate of 12 g/h at a temperature of 350° C. As shown in Table 2, all the mono- and bi-valent metal chloride catalysts provided a t/c-1234ze selectivity higher than 80% and a t/c-1233zd selectivity lower than 20%, indicating those catalysts are more active for 244fa dehydrochlorination than its dehydrofluorination. A HCFC-244fa conversion higher than 90% was achieved over the following catalysts: 10.0 wt % LiCl/C, 10.0 wt % KCl/C, and 10.0 wt % $MgCl_2$/C. On the other hand, the tri-valent iron chloride catalyst exhibited a t/c-1234ze selectivity of about 9% and a t/c-1233zd selectivity of about 61%, which suggests that this catalyst is more active for HCFC-244fa dehydrofluorination than its dehydrochlorination.

TABLE 2

| | HFC-244fa dehydrohalogenation over metal chloride catalysts at 350° C. | | | | |
|---|---|---|---|---|---|
| | Conversion, % | Selectivity, % | | | |
| Catalyst | 244fa | t/c-1234ze | 245fa | t/c-1233zd | unknown |
| 10.0 wt % LiCl/C | 96.2 | 95.2 | 0.0 | 4.4 | 0.4 |
| 10.0 wt % KCl/C | 97.9 | 94.4 | 0.0 | 4.9 | 03 |
| 10.0 wt % $MgCl_2$/C | 99.3 | 92.9 | 0.0 | 6.7 | 0.4 |
| 10.0 wt % $NiCl_2$/C | 89.3 | 93.4 | 0.0 | 5.4 | 1.2 |
| 10.0 wt % $CuCl_2$/C | 28.5 | 83.8 | 0.0 | 13.0 | 3.2 |
| 10.0 wt % $ZnCl_2$/C | 29.4 | 80.8 | 1.0 | 17.0 | 1.2 |
| 10.0 wt % $FeCl_3$/C | 66.8 | 9.4 | 24.3 | 61.4 | 4.9 |

Example 3

HFC-244fa Dehydrohalogenation Over carbon Supported LiCl Catalysts

In Example 3 the effect of LiCl loading in LiCl/C catalysts was investigated. 20 cc of each LiCl/C catalyst was used. HCFC-244fa was passed over each catalyst at a rate of 12 g/h at a temperature of 350° C. Table 3 shows the effect of LiCl loading on the performance of LiCl/C catalysts. One can see the LiCl loading has no significant impact on the HCFC- 244fa conversion and product distributions. The t/c-1234ze selectivity was more than 90% over all the LiCl catalysts investigated. These results indicate that LiCl/C is an excellent catalyst for HCFC-244fa dehydrochlorination and the LiCl loading can be changed in a wide range.

TABLE 3

LiCl loading on during 244fa dehydrohalogenation at 350° C.

| LiCl loading, wt % | Conversion, % | Selectivity, % | | | |
|---|---|---|---|---|---|
| | 244fa | t/c-1234ze | 245fa | t/c-1233zd | unknown |
| 0.5 | 99.5 | 94.6 | 0.0 | 4.2 | 1.2 |
| 1.0 | 99.5 | 94.3 | 0.0 | 4.3 | 1.4 |
| 2.5 | 99.6 | 94.4 | 0.0 | 4.2 | 1.4 |
| 5.0 | 99.0 | 94.2 | 0.0 | 5.2 | 0.6 |
| 10.0 | 96.2 | 95.2 | 0.0 | 4.4 | 0.4 |
| 20.0 | 98.2 | 93.4 | 0.0 | 5.9 | 0.8 |

Example 4

HFC-244fa Dehydrohalogenation Over Metal Fluoride Catalysts

In Example 4, a series of mono-, bi-, tri-, and tetra-valent metal fluorides were used as dehydrohalogenation catalysts. 20 cc of each metal fluoride catalyst was used. 244fa was passed over each catalyst at a rate of 12 g/h at a temperature of 350° C. As shown in Table 4, the mono- and bi-valent metal fluoride catalysts provided a t/c-1234ze selectivity higher than 90% and a t/c-1233zd selectivity lower than 10%, while the tri and tetra-valent metal fluoride catalysts exhibited a t/c-1234ze selectivity lower than 25% and a t/c-1233zd selectivity higher than 65%. These results indicate the mono- and bi-valent instead of tri- and tetra-valent metal fluoride catalysts are excellent ones for 244fa dehydrochlorination.

TABLE 4

HFC-244fa dehydrohalogenation over metal fluoride catalysts at 350° C.

| Catalyst | Conversion, % | Selectivity, % | | | |
|---|---|---|---|---|---|
| | 244fa | t/c-1234ze | 245fa | t/c-1233zd | unknown |
| 1.0 wt % LiF/C | 99.1 | 94.6 | 0.0 | 4.0 | 1.4 |
| 1.0 wt % MgF$_2$/C | 99.2 | 94.4 | 0.0 | 3.8 | 1.8 |
| AlF$_3$ | 100.0 | 21.8 | 0.0 | 77.3 | 0.9 |
| CeF$_4$ | 69.3 | 4.9 | 21.3 | 65.4 | 8.4 |

Example 5

HFC-244fa Dehydrohalogenation Over Zero-Valent Non-Precious Metal Catalysts

In Example 5, a series of zero-valent non-precious metals supported on carbon were used as dehydrohalogenation catalysts. 20 cc of each metal catalyst was used. HCFC-244fa was passed over each catalyst at a rate of 12 g/h at a temperature of 350° C. As shown in Table 5, all the metal catalysts provided a t/c-1234ze selectivity higher than 90% and a t/c-1233zd selectivity lower than 10%, which indicates that those metal catalysts are more active for HCFC-244fa dehydrofl-horination than its dehydrofluorination. Among the metals investigated, Co exhibited the highest activity.

TABLE 5

HFC-244fa dehydrohalogenation over metal-based catalysts at 350° C.

| Catalyst | Conversion, % | Selectivity, % | | | |
|---|---|---|---|---|---|
| | 244fa | t/c-1234ze | 245fa | t/c-1233zd | unknown |
| 0.5 wt % Fe/C | 86.0 | 94.1 | 0.0 | 5.1 | 0.8 |
| 0.5 wt % Co/C | 94.3 | 94.5 | 0.0 | 4.9 | 0.6 |
| 0.5 wt % Ni/C | 71.6 | 93.2 | 0.0 | 6.2 | 0.6 |
| 0.5 wt % Cu/C | 90.6 | 94.6 | 0.0 | 4.4 | 1.0 |

Although the present invention has been described and exemplified above in connection with certain preferred embodiments, it is not necessarily limited to these examples and embodiments. The scope of the invention is defined in accordance with the claims presented hereinbelow and/or presented hereinafter.

What is claimed is:

1. A process for the production of fluorinated olefins comprising exposing, in a gas phase, a fluorinated and chlorinated alkane stream comprising HCFC-244fa to conditions effective to convert at least about 70% by weight of said alkane stream to an olefin stream comprising HFO-1234ze, wherein said exposing step comprises exposing said alkane stream to a catalyst selected from the group consisting of LiF, NaF, KF, MgF$_2$, NiF$_2$, LiCl, KCl, MgCl$_2$, NiCl$_2$, CuCl$_2$, ZnCl$_2$, NaCl, CsCl, CsF, activated carbon, Fe, Co, Ni, Cu, and combinations of two or more of these, wherein said catalyst is optionally supported by a substrate selected from the group consisting of carbon, activated carbon, graphite, fluorinated graphite, and combinations of two or more of these.

2. The process of claim 1 wherein said exposing step comprises conditions effective to convert at least about 80% by weight of said alkane stream comprising HCFC-244fa to said olefin stream comprising HFO-1234ze.

3. The process of claim 1 wherein said exposing step comprises conditions effective to convert at least about 90% by weight of said alkane stream comprising HCFC-244fa to said olefin stream comprising HFO-1234ze.

4. The process of claim 1 wherein said HFO-1234ze comprises trans-HFO-1234ze.

5. The process of claim 1 wherein said HFO-1234ze comprises cis-HFO-1234ze.

6. The process of claim 1 wherein said HFO-1234ze consists essentially of a mixture of cis-HFO-1234ze and trans-HFO-1234ze.

7. The process of claim 1 wherein said catalyst is LiCl supported on by a carbon substrate.

8. The process of claim 1 wherein said exposing step is conducted under a reaction temperature condition of from about 300° C. to less than about 400° C.

9. The process of claim 1 wherein said exposing step is conducted under a reaction temperature condition of from about 325° C. to about 375° C.

10. The process of claim 1 wherein said exposing step is conducted under a reaction temperature condition of about 350° C.

11. The process of claim 1 wherein said exposing step is conducted under a reaction pressure condition of from about 5 ton to about 200 psig.

* * * * *